(12) United States Patent
Hsieh et al.

(10) Patent No.: US 9,140,857 B2
(45) Date of Patent: Sep. 22, 2015

(54) DOUBLE-SIDED GRATING WAVEGUIDE BIOSENSOR

(71) Applicant: NATIONAL CHUNG CHENG UNIVERSITY, Chiayi (TW)

(72) Inventors: Wen-Hsin Hsieh, Chiayi (TW); Lai-Kwan Chau, Chiayi (TW); Hsun-Yuan Li, Chiayi (TW); Wei-Chun Hsu, Chiayi (TW)

(73) Assignee: National Chung Cheng University, Chia-Yi (TW)

( * ) Notice: Subject to any disclaimer, the term of this patent is extended or adjusted under 35 U.S.C. 154(b) by 48 days.

(21) Appl. No.: 14/057,469

(22) Filed: Oct. 18, 2013

(65) Prior Publication Data
US 2014/0112613 A1  Apr. 24, 2014

(30) Foreign Application Priority Data
Oct. 19, 2012  (TW) .............................. 101138833 A (51) Int. Cl.
  *G02B 6/00* (2006.01)
  *G02B 6/34* (2006.01)
  *G01N 21/77* (2006.01)
  *G02B 6/124* (2006.01)

(52) U.S. Cl.
  CPC .............. *G02B 6/34* (2013.01); *G01N 21/7743* (2013.01); *G02B 6/124* (2013.01)

(58) Field of Classification Search
  CPC ....... G02B 6/34; G02B 6/124; G01N 21/7743
  USPC .......................................................... 385/12
  See application file for complete search history.

(56) References Cited

U.S. PATENT DOCUMENTS

| 5,677,769 | A  | * | 10/1997 | Bendett ........................ 356/440 |
| 6,078,705 | A  | * | 6/2000  | Neuschafer et al. ............ 385/12 |
| 6,395,558 | B1 | * | 5/2002  | Duveneck et al. ............ 436/172 |
| 8,349,605 | B1 | * | 1/2013  | Lear et al. .................. 435/288.7 |
| 2009/0187350 | A1 | * | 7/2009  | Chau et al. ...................... 702/19 |
| 2013/0102090 | A1 | * | 4/2013  | Lear et al. ..................... 436/501 |

OTHER PUBLICATIONS

Schmitt et al., (Evanescent field Sensors Based on Tantalum Pentoxide Waveguides—A Review, Sensors 2008, 8, 711-738; "Schmitt").*
Chuen-Lin Tien; Tsai-Wei Lin; Hung-Yi Hsu; Li-Chieh Chen; Yu-Chung Chen; Wen-Feng Liu, "Double-sided polishing long period fiber grating sensors for measuring liquid refractive index," Communications and Photonics Conference and Exhibition (ACP), 2009 Asia , vol. 2009-Supplement, No., pp. 1,6, Nov. 2-6, 2009.*

* cited by examiner

*Primary Examiner* — Peter Radkowski
(74) *Attorney, Agent, or Firm* — Saliwanchik, Lloyd & Eisenschenk (57) ABSTRACT

Disclosed is a double-sided grating waveguide biosensor. The double-sided grating waveguide biosensor is used to sense the properties of a sample solution. The double-sided grating waveguide biosensor comprises a sequential stack of a plastic grating having a grating part, a waveguide layer having a double-sided grating structure, and a channel chip. Furthermore, the sample solution is guided into the channel chip; the light beam is coupled into the waveguide layer via the double-sided grating structure, propagates in the waveguide layer, and penetrates outward. The double-sided waveguide biosensor detects the properties of the sample solution via a variation of a light beam intensity of the outgoing light beam.

12 Claims, 12 Drawing Sheets

DOUBLE-SIDED GRATING WAVEGUIDE BIOSENSOR

CROSS-REFERENCE TO RELATED APPLICATION

This application claims the benefit under 35 U.S.C. §119 of Taiwanese Patent Application No. 101138833, filed Oct. 19, 2012, which is hereby incorporated by reference in its entirety.

BACKGROUND

1. Field of the Invention

The present invention relates to a biosensor, and particularly, a double-sided grating waveguide biosensor with a double-sided grating structure.

2. Description of the Related Art

In recent years, the biomedical sensing industry pays more and more attention to the accuracy and convenience when conducting a specific detection, while optical biosensors are exactly able to meet these requirements. Due to the fact that the development of optical waveguide devices gradually becomes more mature, people begin to utilize optical waveguide devices in detecting. Conventionally, an optical waveguide biosensor is either equipped with a prism or a grating as the coupling device to couple in a light beam into the waveguide layer. The detecting purpose is achieved by measuring the variations of the angle and the wavelength of the light beam source. However, measuring the variations of the angle and the wavelength of the light beam requires complex measurement instruments.

Additionally, manufacturing of grating biosensors are rather difficult, because grating is not easy to produce. Currently, the conventional manufacturing methods of grating biosensors are imprinting, ion erosion, or the holographic technique. However, these methods are too complex to mass-produce. Besides, the grating biosensors manufactured by these three methods are all single-sided.

BRIEF SUMMARY

Based on the problems of the prior arts, one of the objects of the present invention is to provide a double-sided grating waveguide biosensor to detect properties of a sample solution. The present invention provides a waveguide layer comprising a double-sided grating structure to achieve the goal of effectively coupling a light beam within the preset range into the waveguide layer to perform a detecting. Moreover, a new manufacturing method of the double-sided grating waveguide biosensor is applied to realize the purpose of mass production and cost reduction.

Thus, the present invention provides a double-sided grating waveguide biosensor to sense the properties of a sample solution. The double-sided grating waveguide biosensor at least comprises a plastic grating, a waveguide layer, and a channel chip. The material of the plastic grating is, for example, cyclic-olefin copolymers (COCs), polycarbonate, acrylic, polypropene, or other suitable plastic material with high transparency. One surface of the plastic grating is provided with a grating part. The waveguide layer is located on the surface with the grating part of the plastic grating, and part of the waveguide layer is located on the grating part to form a double-sided grating waveguide structure. Furthermore, the double-sided grating structure comprises two waveguide grating parts corresponding to each other. The material of the waveguide layer is, for example, titanium dioxide, zirconium dioxide, silicon dioxide, titanium sesquioxide, tantalum pentoxide, zinc oxide, or suitable material with high refraction index and stable chemical properties, to increase the sensing sensitivity and range of the double-sided grating waveguide biosensor.

Additionally, the channel chip is installed on the waveguide layer such that the sample solution can be guided into a storage space of the channel chip. When the light beam is coupled into the waveguide layer via the double-sided grating structure and propagates along the waveguide layer, the double-sided grating waveguide biosensor of the present invention detects the properties of the sample solution via the variations of a light beam intensity of the light beam penetrating out of the waveguide layer.

Additionally, the double-sided grating waveguide biosensor of the present invention further comprises a recognition molecule layer fixedly bonded to the surface of the waveguide layer between the waveguide layer and the channel chip. The recognition molecule layer is designed to interact with the sample solution such that the double-sided grating waveguide biosensor of the present invention can have a good limit of detection in sensitivity when it is used to perform a measurement.

Additionally, the plastic grating of the double-sided grating waveguide biosensor of the present invention has a plurality of gaps. The plurality of gaps are located between the plastic grating and the waveguide layer.

Additionally, the double-sided grating structure is provided with one or both of a coupling position and an angle of coupling ranged from −90 to 90 degrees. A distance between the coupling position and a terminal of the double-sided grating structure is within 0 to 2 centimeters. Besides, the ranges of the coupling position and the angle of coupling and the coupling position and the angle of coupling of the peak light beam intensity do not change with the variations of the refraction index. Furthermore, the detecting sensitivity does not change with the variations of the angle of coupling and the coupling position.

Thus, one of the features of the detecting method by using the double-sided grating waveguide biosensor of the present invention is to couple in the light beam into the waveguide layer of the double-sided grating structure and to detect the light beam intensity of the coupling output, such that the light beam can possess the coupling capability within a range. Within this range, the sensitivity of the double-sided grating waveguide biosensor does not change with the different selections of the angle of coupling and the coupling position. Another feature of the sensing method by using the double-sided grating waveguide biosensor of the present invention is to simplify the complexity of the detecting processes by measuring the light beam intensity of the coupling output.

As above-mentioned, the double-sided grating waveguide biosensor of the present invention may have one or more characteristics and advantages as described below:

(1) The detection sensitivity and range of the double-sided grating waveguide biosensor of the present invention is enhanced by means of the high refraction index and the stable chemical characteristics of the material of the waveguide layer.

(2) With the double-sided grating structure of the recognition layer and the waveguide layer, the double-sided grating waveguide biosensor of the present invention can have a good limit of detection in sensitivity when it is used to perform a measurement.

(3) The light beam is provided with the coupling capability within a range through coupling in the light beam into the waveguide layer of the double-sided grating structure and detecting the light beam intensity of the coupling output. Within this range, the detection sensitivity of the double-sided grating waveguide biosensor of the present invention does not change with the different selections of the angle of coupling and the coupling position.

(4) The complexity of the sensing processes is simplified through detecting the light beam intensity of the coupling output.

DETAILED DESCRIPTION

Figure 1:
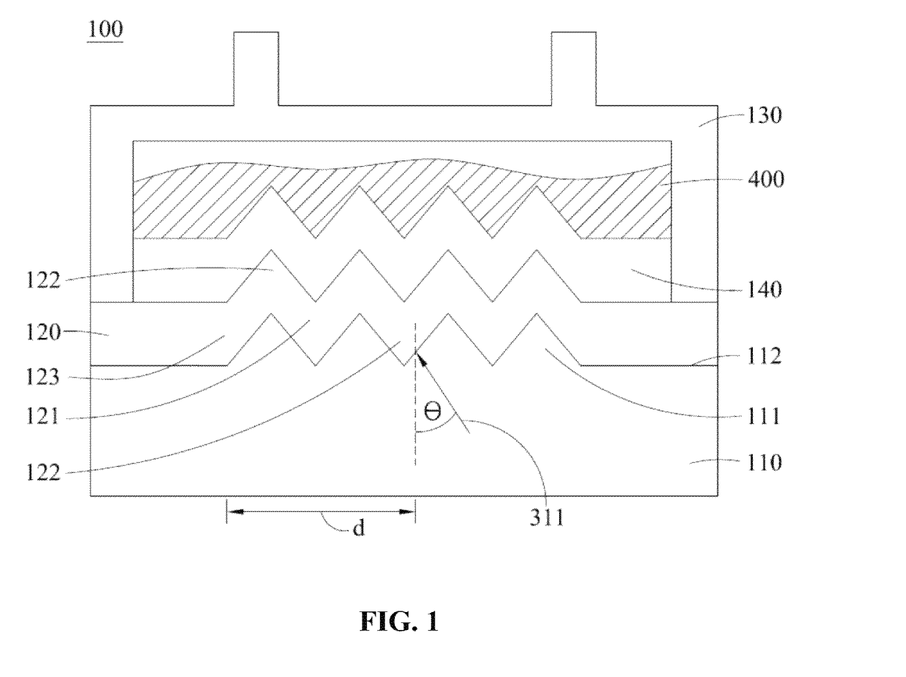
FIG. 1 is the structure diagram showing a double-sided grating waveguide biosensor according to the first preferred embodiment of the present invention.
Figure 2:
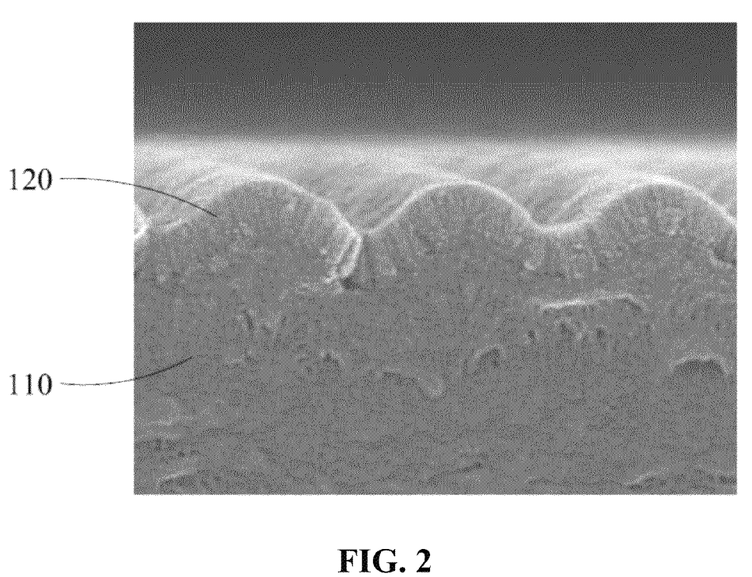
FIG. 2 is a SEM graph of the plastic grating and the waveguide layer which are shown on FIG. 1.

Referring to FIGS. 1-2, FIG. 1 is the structure diagram showing a double-sided grating waveguide biosensor according to the first preferred embodiment of the present invention, FIG. 2 is a SEM micrograph of the plastic grating and the waveguide layer which shown on FIG. 1. As shown in FIGS. 1-2, the double-sided grating waveguide biosensor of the present invention at least comprises a plastic grating 110, a waveguide layer 120, a channel chip 130, and further comprises, for example, a recognition molecule layer 140. Furthermore, the material of the plastic grating is, for example, cyclic-olefin copolymers, polycarbonate, acrylic, polypropene, or other suitable plastic material with high transparency. A surface 112 of the plastic grating 110 is provided with a grating part 111, and the grating part 111 and the plastic grating 110 are generated together in one step.

Additionally, a waveguide layer 120 is located on the surface 112, and part of the waveguide layer 120 is located on the grating part 111 to form a double-sided grating waveguide structure 121. Besides, the double-sided grating structure 121 comprises two waveguide grating parts 122 corresponding to each other. The double-sided grating structure 121 is designed to guide the external light beam into the waveguide layer 120. When the surface effective refraction index of the waveguide layer 120 is changed, the optical properties will change accordingly. These optical properties can be, for example, the angle of coupling, the coupling energy, the wavelength, or the phase, etc. The optical property can also be, for example, the light beam intensity of the light beam penetrated outward the waveguide layer 120. Besides, the material of the waveguide layer 120 can be, for example, titanium dioxide, zirconium dioxide, silicon dioxide, titanium sesquioxide, tantalum pentoxide, zinc oxide, or other material which has higher refraction index than that of plastic grating 110.

Additionally, the waveguide layer 120 can be, for example, deposited on the surface 112 of the plastic grating 110. The deposit method can be, for example, sputtering coating, evaporation, dip coating, spin coating, or any method which enables the waveguide layer 120 to be uniformly deposited on the surface 112 of the plastic grating 110. Thus, the waveguide layer 120 can be, for example, deposited smoothly and uniformly on the plastic grating 110. Since the grating part 111 is located on the surface 112 of the plastic grating 110, the waveguide layer 120 on the grating part 111 can be provided with the double-sided grating structure 121 which comprises two waveguide grating parts 122 corresponding to each other. Furthermore, the height of the grating of each the two waveguide grating parts 122 are roughly equal to that of the grating part 111.

Thus, one of the features of the double-sided grating waveguide biosensor 100 of the present invention is that the detection sensitivity and range of the double-sided grating waveguide biosensor 100 of the present invention is enhanced by means of the high refraction index and the stable chemical characteristics of the material of the waveguide layer 120.

Figure 3:
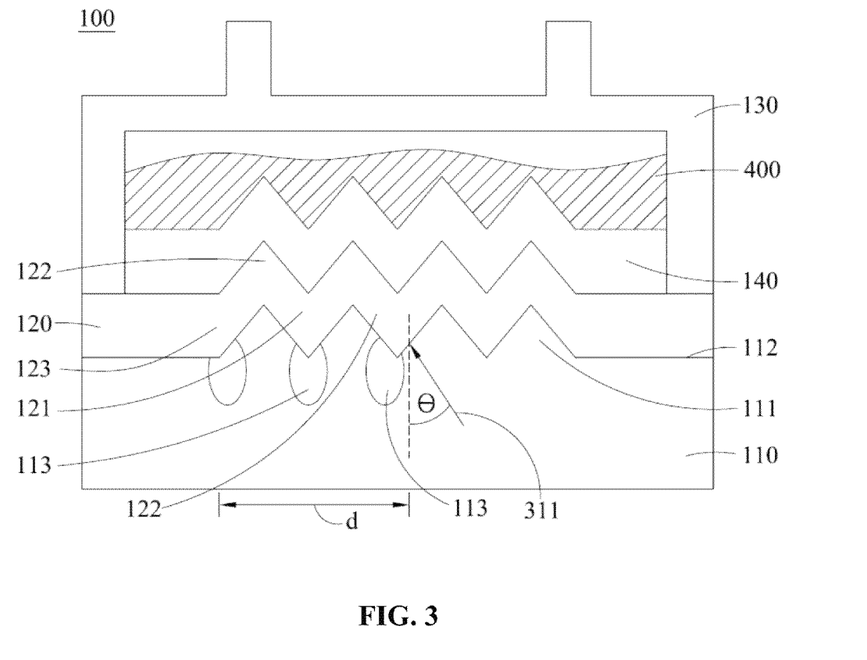
FIG. 3 is the structure diagram showing a double-sided grating waveguide biosensor according to the second preferred embodiment of the present invention.
Figure 4:
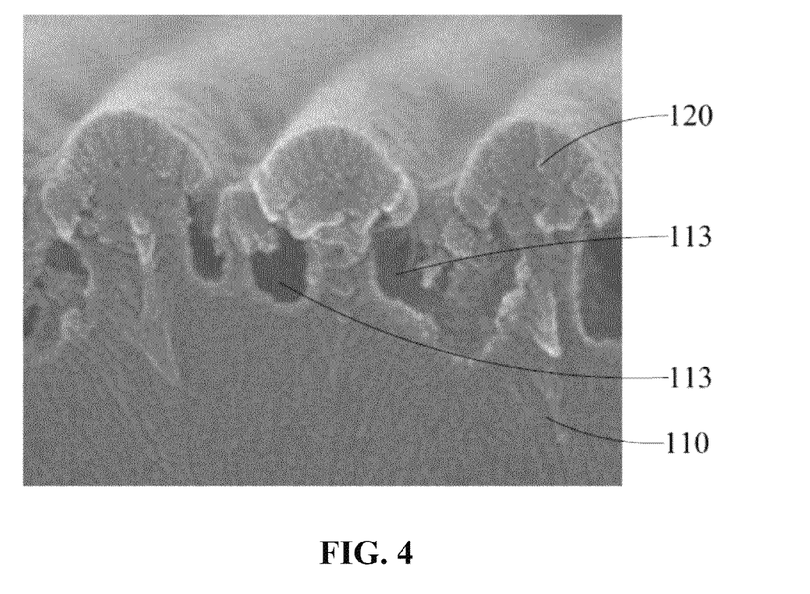
FIG. 4 is a SEM graph of the plastic grating and the waveguide layer which are shown on FIG. 3.

Additionally, further referring to FIGS. 3-4, FIG. 3 is the structure diagram showing a double-sided grating waveguide biosensor according to the second preferred embodiment of the present invention, FIG. 4 is a SEM micrograph of the plastic grating and the waveguide layer which shown on FIG. 3. The second preferred embodiment of the double-sided grating waveguide biosensor of the present invention shown on FIG. 3 is similar to the first preferred embodiment of the double-sided grating waveguide biosensor shown on FIG. 1. The difference between them is the plastic grating 110 of the second preferred embodiment has a plurality of gaps 113, wherein the gaps 113 are formed on the surface 112 of the plastic grating 110 and located between the plastic grating 110 and the waveguide layer 120 to further enhance the detecting sensitivity of the double-sided grating waveguide biosensor 100.

Additionally, the channel chip 130 is, for example, located on the waveguide layer 120 such that a user can guide in a sample solution 400 and use the double-sided grating waveguide biosensor 100 of the present invention to detect the properties, for example the refraction index, of the sample solution 400. Besides, the user can make use of the properties of the sample solution 400 to decide the composition, concentration, or other properties of the sample solution 400. Furthermore, the channel chip 130 can be, for example, provided with an outer shell and a storage space. The storage space is used to store the sample solution 400 for detection. The material of the outer shell is, for example, cyclic-olefin copolymers, polycarbonate, acrylic, polypropene, or other suitable plastic material with high transparency. Besides, the outer shell can be, for example, provided with holes to guide the sample solution 400 into the storage space or guide it out.

Based on the properties, for example the refraction index, of different sample solutions 400, the double-sided grating waveguide biosensor 100 of the present invention detects the different light beam intensities of the coupling outcomes. Thus, the properties of the sample solution 400 can be analyzed based on the corresponding relationship between the refraction index and the light beam intensity.

Figure 5:
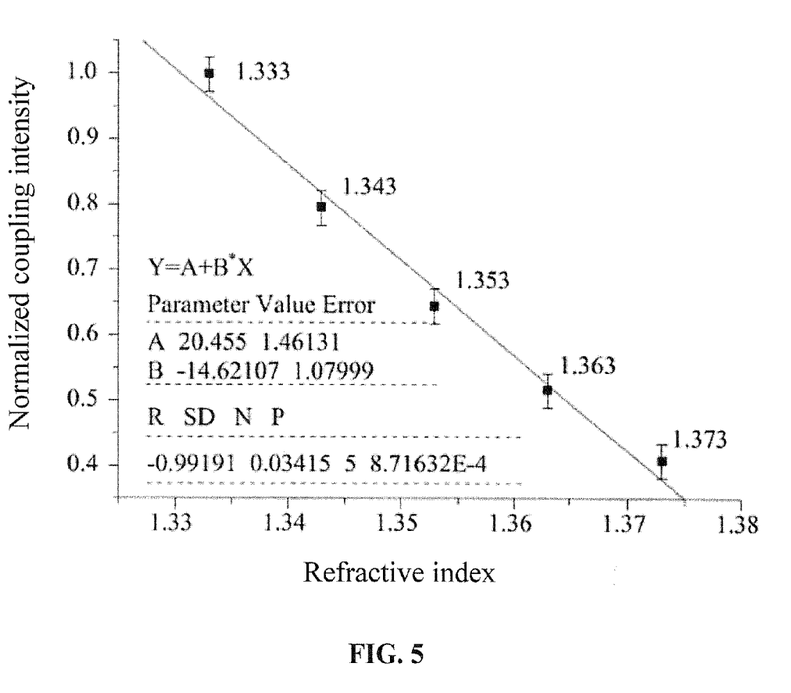
FIG. 5 is the relationship diagram showing the light beam intensity of the coupling outcome and the refraction index of a double-sided grating waveguide biosensor according to the second preferred embodiment of the present invention.

Numerical experimental data are provided to confirm that the double-sided grating waveguide biosensor 100 of the present invention can derive the refraction index of the sample solution 400 by detecting the light beam intensity. Referring to FIG. 5, FIG. 5 is the relationship diagram showing the light beam intensity of the coupling outcome and the refraction index of a double-sided grating waveguide biosensor according to the preferred embodiment of the present invention. As shown in FIGS. 1 and 5, the sucrose solutions of refraction indices of 1.343, 1.353, 1.363, and 1.373 and the deionized (DI) water are guided into the channel chip, and then a laser light beam is guided into the waveguide layer 120 to detect the laser light beam intensity after the light beam is coupled with the waveguide layer 120. The material of the waveguide layer 120 is titanium dioxide.

Furthermore, the first step of the sensing processes is, for example, guided in the deionized water into the channel chip 130, and then the laser light beam is guided into the waveguide layer 120. Afterward, a syringe pump, for example, is used to push the sucrose solution of the refraction index of 1.343 into the channel chip 130, and then the sucrose solutions of the refraction indices of 1.353, 1.363, and 1.373 are injected into the channel chip 130 sequentially in a 1 minute interval. Finally, the deionized water is injected into the channel chip 130 again and held for 2 minutes. In FIG. 5 the horizontal axis is the refraction index of the sample solution 400, while the vertical axis is the processed signal strength of the light beam intensity of the coupling outcome. It can be observed in FIG. 5 that the sensor resolution of the double-sided grating waveguide biosensor 100 of the second preferred embodiment of the present invention can reach up to $5.13 \times 10^{-6}$ refractive index unit (RIU). Besides, the detecting sensitivity of the double-sided grating waveguide biosensor of the second preferred embodiment, which has gaps located between the plastic grating and the waveguide layer, is greater than that of the first preferred embodiment. Thus, the processed signal strength can be used to obtain the refraction index of the sample solution 400 and further derive the properties of the sample solution 400.

Additionally, the double-sided grating waveguide biosensor 100 of the present invention further comprises the recognition molecule layer 140 fixedly bonded to the surface of the waveguide layer 120 between the waveguide layer 120 and the channel chip 130. The recognition molecule layer 140 is designed to interact with the sample solution 400 such that the detection sensitivity of the double-sided grating waveguide biosensor 100 of the present invention can be further increased. Besides, the material of the recognition molecule layer 140 can be, for example, an antibody molecule or other suitable recognition molecules.

Figure 6:
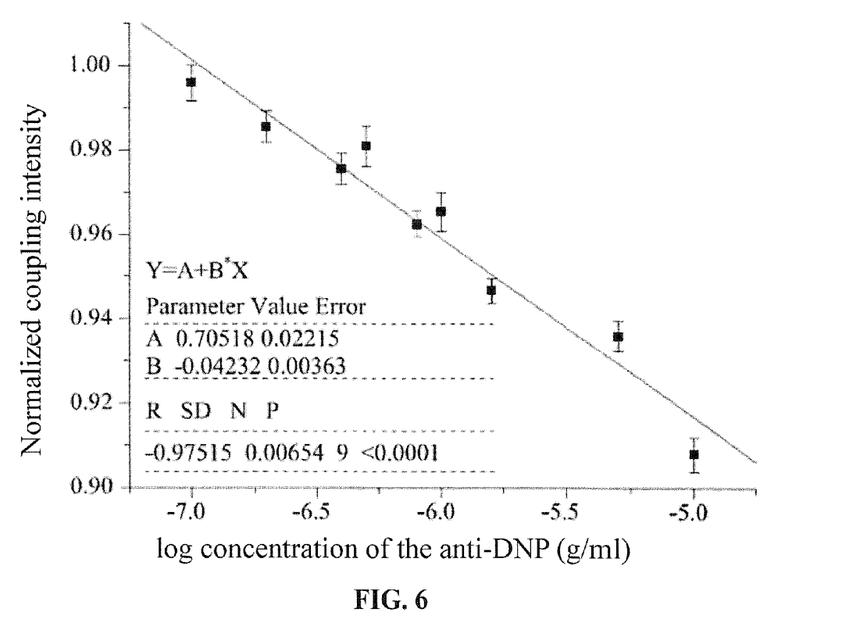
FIG. 6 is a relationship diagram showing the light beam intensity of the coupling outcome and the concentration of the sampling solution showing a double-sided grating waveguide biosensor with a recognition molecule layer according to the first preferred embodiment of the present invention.

Numerical experimental data are provided to confirm that the detection sensitivity of the double-sided grating waveguide biosensor 100 of the present invention can be increased. First, the phosphate buffer solution (PBS) is guided into the channel chip 130, and then the syringe pump is used to pump in the anti-dinitrophenyl antibody (anti-DNP) solution with the density of $1 \times 10^{-7}$ g/cm³ into the channel chip 130. Afterward, the concentration of the anti-DNP solution is elevated and injected into the channel chip 130 in every 30 minutes, until the concentration of the anti-DNP solution reaches $1 \times 10^{-5}$ g/cm³. Referring to FIG. 6, FIG. 6 is a relationship diagram showing the light beam intensity of the coupling outcome and the concentration of the sampling solution of a double-sided grating waveguide biosensor with the recognition molecule layer according to the first preferred embodiment of the present invention. In FIG. 6 the horizontal axis is the concentration of the sample solution, while the vertical axis is the processed signal strength of the light beam intensity of the coupling outcome. As shown in FIGS. 1 and 6, the double-sided grating waveguide biosensor 100 of the present invention can reach the limit of detection (LOD) of $7.81 \times 10^{-8}$ g/cm³.

Thus, one of the features of the double-sided grating waveguide biosensor 100 of the present invention is that the double-sided grating waveguide biosensor 100 of the present invention can have a good limit of detection when performing a detection with the help of the double-sided grating structure 121 of the waveguide layer 20 and the recognition molecule layer 140.

Figure 7:
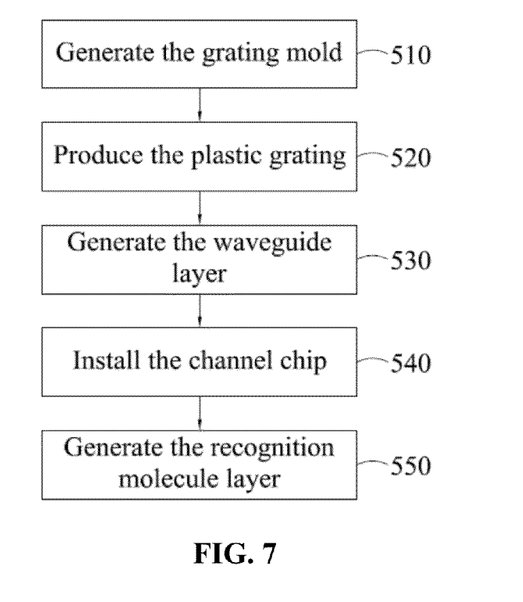
FIG. 7 is a flow diagram showing the manufacturing method of a double-sided grating waveguide biosensor according to the preferred embodiment of the present invention.
Figure 8A:
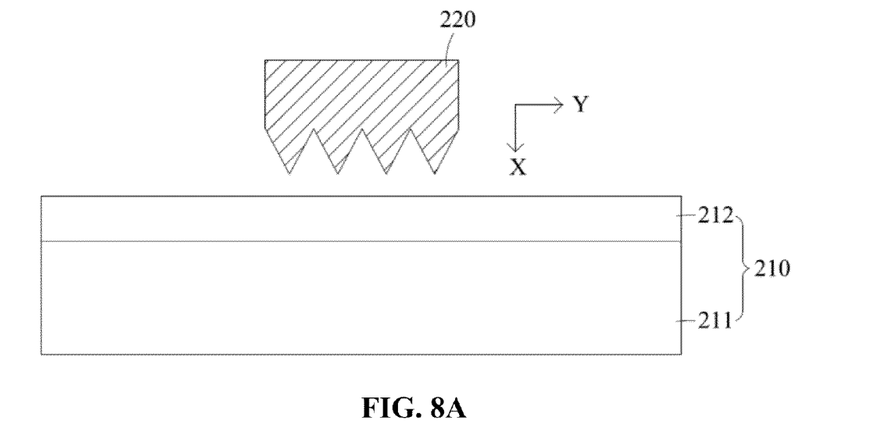
FIGS. 8a-8c are processing sectional diagrams showing the imprinting of the grating structure of a double-sided grating waveguide biosensor according to the preferred embodiment of the present invention.
Figure 8B:
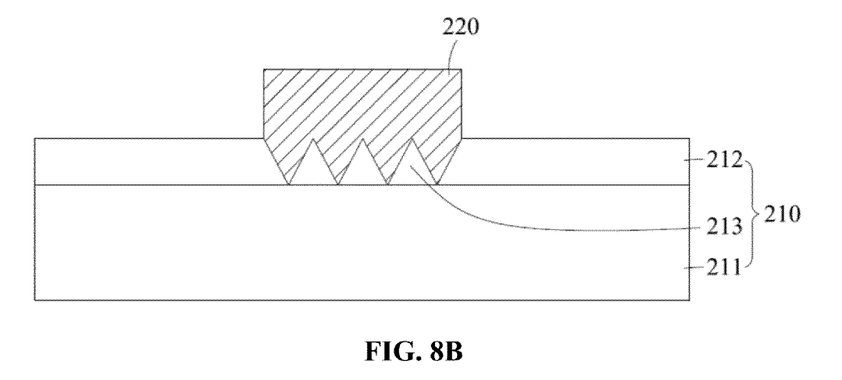
Figure 8C:
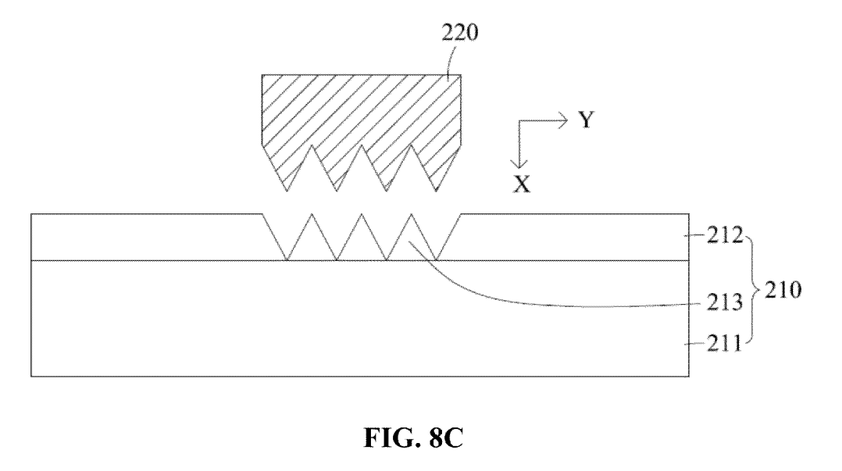
Figure 9:
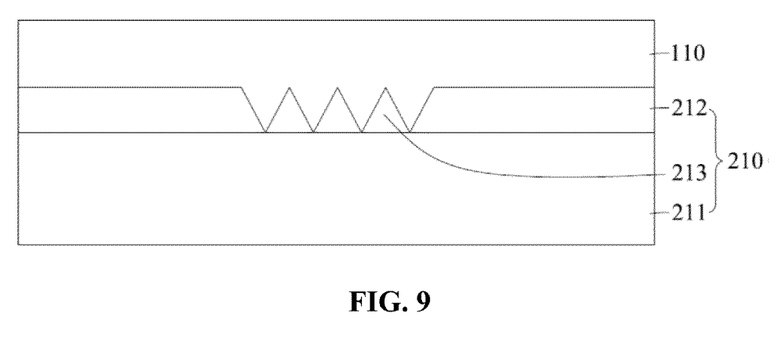
FIG. 9 is a state diagram showing the manufacturing of the plastic grating of a double-sided grating waveguide biosensor according to the preferred embodiment of the present invention.

Referring to FIGS. 7 to 9, FIG. 7 is a flow diagram showing the manufacturing method of a double-sided grating waveguide biosensor according to the preferred embodiment of the present invention. FIGS. 8a-8c are processing sectional diagrams showing the imprinting of the grating structure of a double-sided grating waveguide biosensor according to the preferred embodiment of the present invention. FIG. 9 is a state diagram showing the manufacturing of the plastic grating of a double-sided grating waveguide biosensor according to the preferred embodiment of the present invention. As shown in FIG. 1 and FIGS. 7 to 9, the manufacturing method of the double-sided grating waveguide biosensor 100 of the present invention begin with, for example, generating a grating mold 210 (Step 510). Specifically, generate a sol-gel layer 212 on a substrate 211 by, for example, spread-coating the sol-gel over the substrate 211 made of hard material. Afterward, utilize a grating master mold 220 with the grating master structure to imprint the grating structure 213 on the sol-gel layer 212. Furthermore, vacuum-pumping or high temperature baking, for example, can be used to harden the sol-gel layer 212 and remove the bubbles within the sol-gel layer 212. Finally, the grating mold 210 is generated after the grating master mold 220 is removed.

When imprinting the grating structure 213, for example, the grating master mold 220 is first located above the sol-gel layer 212, and then pressed into the sol-gel layer in the x-direction. Thus, the grating structure 213 is generated on the sol-gel layer 212. Remove the grating master mold 220 away from the sol-gel layer 212 in the opposite of the x-direction and wait until the sol-gel layer is frozen, the grating mold is generated. After the grating master mold 220 is removed, we can proceed to, for example, the modifications of the grating mold 210.

After the grating mold 210 is generated, the next step is to produce the plastic grating 110 (Step 520). Specifically, the grating mold 210 is utilized to perform a shaping on a plastic material to produce the plastic grating 110 which comprises the grating part 111 on the surface 112. Among which, the shaping process of the plastic material can be the injection molding, the injection compression, the hot pressing, the extrusion molding, the vacuum shaping, or other plastic shaping methods. After the plastic material is shaped into the plastic grating 110, the grating mold 210 is separated from the plastic grating 110 to produce the plastic grating 110 with the grating part 111. Besides, the plastic material can be, for example, cyclic-olefin copolymers, polycarbonate, acrylic, polypropene, or other suitable plastic material with high transparency. Steps 510 and 520 are the flow steps to produce the plastic grating of the double-sided grating waveguide biosensor 100 of the present invention.

Thus, one of the features of the double-sided grating waveguide biosensor 100 of the present invention is that the plastic grating 110 can be mass-produced to reduce the cost by using the grating mold 210 to perform the shaping of the plastic material.

After the plastic grating 110 is generated, the next step is to generate the waveguide layer 120 on the plastic grating 110 (Step 530). Furthermore, the waveguide layer 120 is generate on the surface 112 with the grating part 111 of the plastic grating 110, and part of the waveguide layer 120 is located on the grating part 111 to form a double-sided grating waveguide structure 121. The waveguide layer 120 can be, for example, deposited on the plastic grating 110. Thus, the double-sided grating structure 121 of the waveguide layer 120 comprises two waveguide grating parts corresponding to each other. Afterward, the channel chip 130 is installed on the waveguide layer 120 (Step 540) to complete the double-sided grating waveguide biosensor 100 of the present invention. After Step 540, the recognition molecule layer 140 can be selectively generated on the waveguide layer 120 (Step 550). After the channel chip 130 is installed, for example, the recognition molecule layer 140 is injected and fixedly bonded to the surface of the waveguide layer 120 between the waveguide layer 120 and the channel chip 130 to enhance the detection sensitivity of the double-sided grating waveguide biosensor 100 of the present invention.

Thus, one of the features of the double-sided grating waveguide biosensor 100 of the present invention is that the double-sided grating waveguide biosensor 100 of the present invention can be mass-produced with the reduced cost by using the grating mold 210 to produce the optical grating 110 and by using the deposit technologies to generate the waveguide layer 120 on the plastic grating 110.

Figure 10:
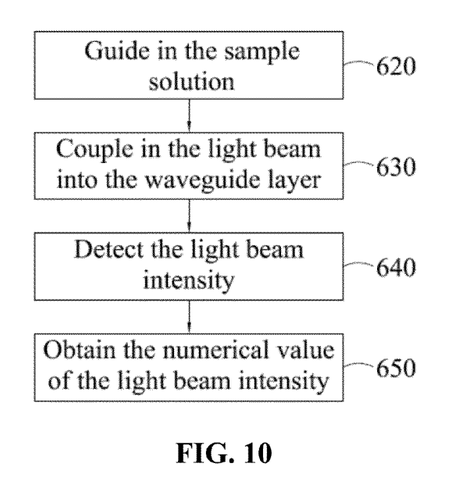
FIG. 10 is a flow diagram showing the detection method of a double-sided grating waveguide biosensor according to the preferred embodiment of the present invention.
Figure 11:
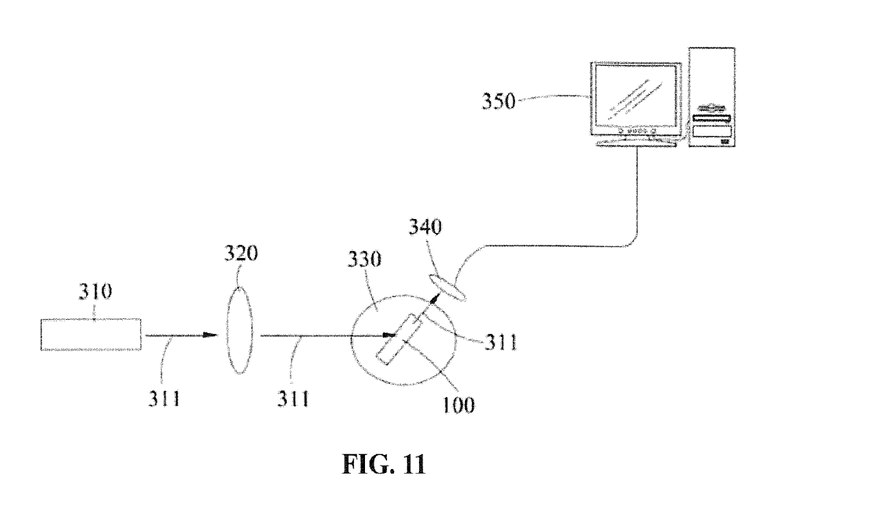
FIG. 11 is a detection system diagram showing a double-sided grating waveguide biosensor according to the preferred embodiment of the present invention.

Referring to FIGS. 10 and 11, FIG. 10 is a flow diagram showing the detection method of a double-sided grating waveguide biosensor according to the preferred embodiment of the present invention. FIG. 11 is a detection system diagram showing a double-sided grating waveguide biosensor according to the preferred embodiment of the present invention. As shown in FIGS. 1, 10, and 11, in the detection method of using the double-sided grating waveguide biosensor 100 of the present invention, the sample solution 400 can be guided into the channel chip 130 of the double-sided grating waveguide biosensor 100 (Step 620). Afterward, a light beam 311 can be coupled into the waveguide layer 120 (Step 630). Specifically, a light source 310 can be used to emit a light beam 110 such as a laser light beam. The light beam is guided into the plastic grating 110 via an optical device 320, and then coupled into the waveguide layer 120 via the double-sided grating structure 121. Furthermore, the optical device 320 can be, for example, a beam splitter, an optical fading lens, a convex lens, or any device which can change the direction or the property of the light beam 311.

Additionally, the double-sided grating waveguide biosensor can be, for example, located on a rotary stage 330. The rotary stage 330 is used to adjust the angle θ of coupling and the coupling position of the light beam 311 when coupling into the waveguide layer 120. Furthermore, the angle θ of coupling and the coupling position within their specific preset ranges do not change with the variations of the refraction index of the sample solution 400. The coupling position and the angle of coupling of the peak light beam intensity do not change with the variations of the refraction index, either. Thus, any of the light beams 311 within the preset range can be effectively coupled into the waveguide layer 120. The angle θ of coupling is ranged from −90 to 90 degrees. The coupling position is located on the double-sided grating structure 121, and the distance d between the coupling position and the terminal 123 of the double-sided grating structure is within 0 to 2 centimeters.

After Step 630, the light beam intensity is detected (Step 640). For example, the light detector 340 is used to detect the intensity of the light beam 311 emitted from the waveguide layer 120 of the double-sided grating waveguide biosensor 100. Afterward, the numerical value of the light beam intensity of the light beam 311 is processed (Step 650). For example, a data processing system 350 is used to process the light beam intensity detected by the light detector 340, such that the user can utilize the variation data of the light beam intensity to calculate the detection sensitivity and analyze the properties of the sample solution 400.

Figure 12:
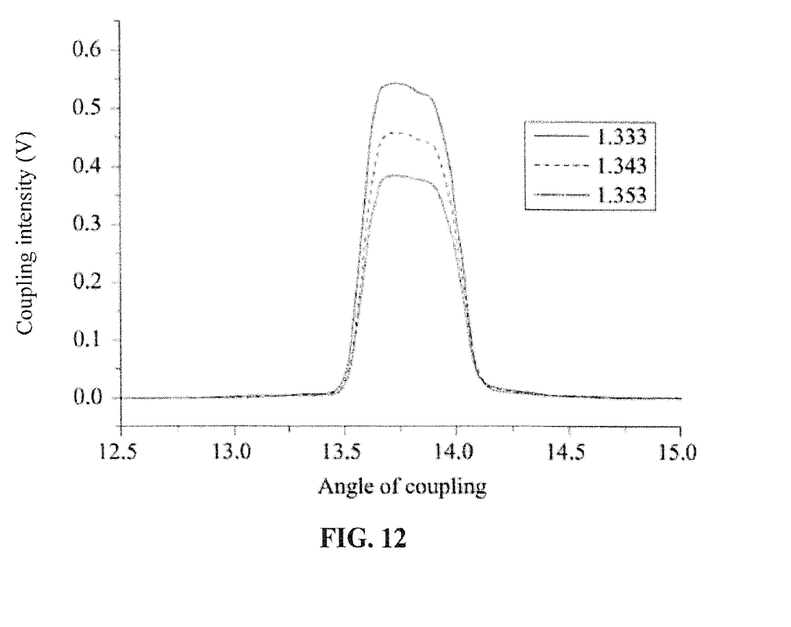
FIG. 12 is a relationship diagram showing the light beam intensities of the sample solutions with different refraction indices and the angle of coupling of a double-sided grating waveguide biosensor according to the preferred embodiment of the present invention.

Numerical experimental data are provided to confirm that the angle θ of coupling and the coupling position within their specific preset ranges do not change with the variations of the refraction index of the sample solution 400 and the light beam 311 is effectively coupled into the waveguide layer 120 in the detection method of the double-sided grating waveguide biosensor 100 of the present invention. Referring to FIG. 12, FIG. 12 is a relationship diagram showing the light beam intensities of the sample solutions with different refraction indices and the angle of coupling of a double-sided grating waveguide biosensor according to the preferred embodiment of the present invention. As shown in FIGS. 1 and 12, the range of the angle θ of coupling remains the same, no matter the refraction index of the sample solution 400 is 1.333, 1.343, or 1.353. In other words, the variations of the refraction index of the sample solution 400 do not change the range of the angle θ of coupling. Besides, the angle of coupling of the peak light beam intensity does not change with the variations of the refraction index of the sample solution 400. The light beam intensity is apparently greater as the angle of coupling is between 13.3° and 14.1°.

Figure 13:
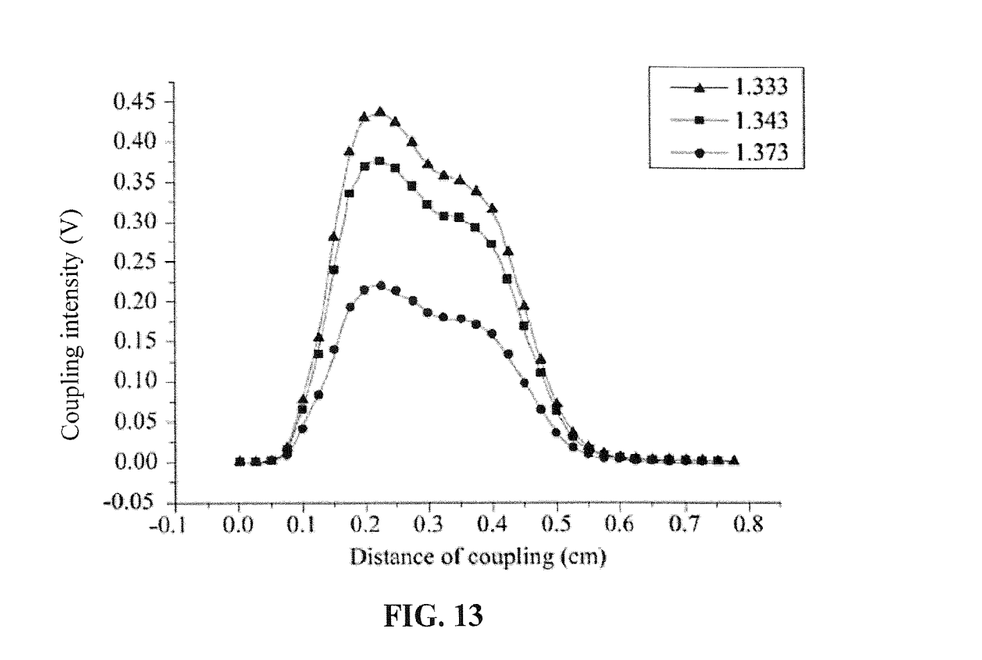
FIG. 13 is a relationship diagram showing the light beam intensities of the sample solution with different refraction indices and the coupling position of a double-sided grating waveguide biosensor according to the preferred embodiment of the present invention.

Referring to FIG. 13, FIG. 13 is a relationship diagram showing the light beam intensities of the sample solution with different refraction indices and the coupling position of a double-sided grating waveguide biosensor according to the preferred embodiment of the present invention. As shown in FIGS. 1 and 13, the light beam can be effectively coupled into the waveguide layer 120, no matter the refraction index of the sample solution 400 is 1.333, 1.343, or 1.373 and where the coupling position is. Thus, the light beam intensity is changed apparently as the distance d between the coupling position and a terminal 123 of the double-sided grating structure 121 is within 0 to 2 centimeters. Besides, the variations of the refraction index of the sample solution 400 do not change the range of the coupling position. Within this range, the angle of coupling of the peak light beam intensity does not change with the variations of the refraction index of the sample solution 400.

Figure 14:
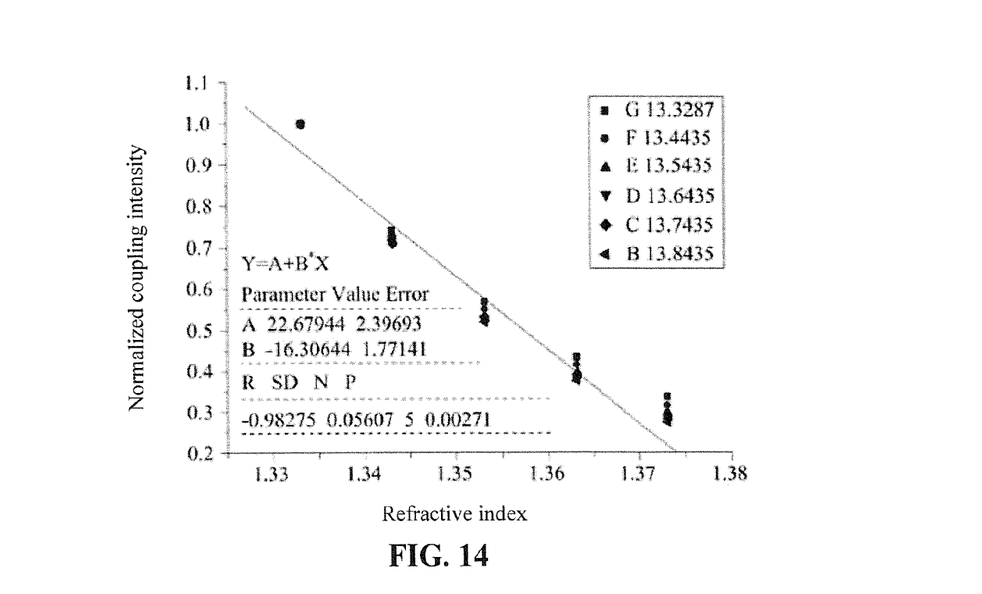
FIG. 14 is a relationship diagram showing the light beam intensities of different angles of coupling and the refraction index of a double-sided grating waveguide biosensor according to the first preferred embodiment of the present invention.

Referring to FIG. 14, FIG. 14 is a relationship diagram showing the light beam intensities of different angles of coupling and the refraction index of a double-sided grating waveguide biosensor according to the first preferred embodiment of the present invention. As shown in FIGS. 1 and 14, the deionized water and the sucrose solutions of refraction indices of 1.343, 1.353, 1.363, or 1.373 are separately guided in the channel chip 130 to carry out the detection. First, the deionized water is injected into the channel chip 130, and then the light beam 311 is coupled into the waveguide layer 120 with the angle of coupling of 13.3287°. Afterward, a syringe pump, for example, is used to push the sucrose solution of the refraction index of 1.343 into the channel chip 130, and follow by sucrose solutions of increasing refraction indices in a 1 minute interval until the sucrose solution of the refraction index of 1.373 is injected. Finally, the deionized water is injected into the channel chip 130 and holds for 2 minutes to complete a detection cycle. Afterward, the angle of coupling is adjusted to 13.4435°, 13.5435°, 13.6435°, 13.7435°, and 13.8435° separately, and then the above detection procedures are repeated. As shown in FIG. 14, the detected signal strength maintains a linear relationship with the refraction index of the sample solution 400. In other words, the detection sensitivity of the double-sided grating waveguide biosensor 100 of the present invention does not change with the variations of the angles of coupling.

Figure 15:
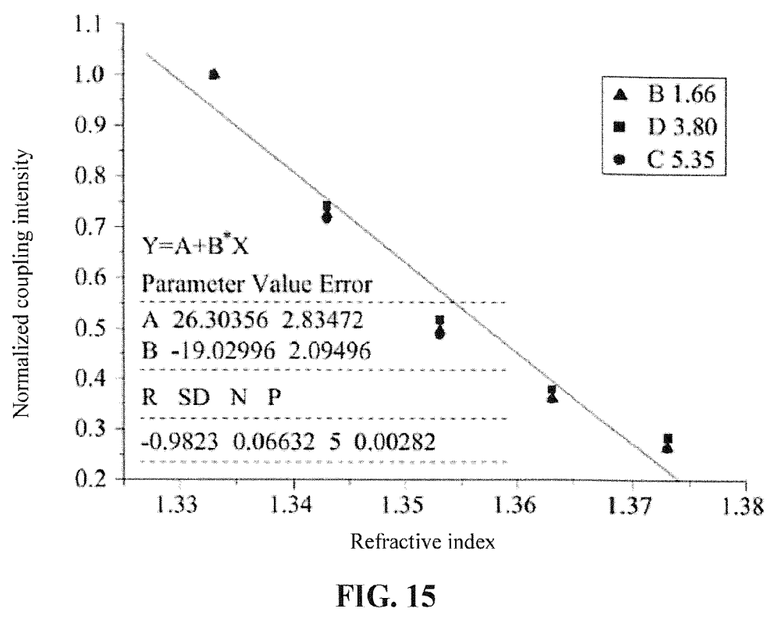
FIG. 15 is a relationship diagram showing the light beam intensities of different coupling positions and the refraction index of a double-sided grating waveguide biosensor according to the first preferred embodiment of the present invention.

Referring to FIG. 15, FIG. 15 is a relationship diagram showing the light beam intensities of different coupling positions and the refraction index of a double-sided grating waveguide biosensor according to the first preferred embodiment of the present invention. As shown in FIGS. 1 and 15, the deionized water and the sucrose solutions of refraction indices of 1.343, 1.353, 1.363, or 1.373 are separately guided in the channel chip 130 to carry out the detection. First, the deionized water is injected into the channel chip 130, and then the light beam 311 is coupled into the waveguide layer 120 at the coupling position of 1.66 mm away from the terminal 123 of the double-sided grating structure 121. Afterward, a syringe pump, for example, is used to push the sucrose solution of the refraction index of 1.343 into the channel chip 130, and follow by sucrose solutions of increasing refraction indices in a 1 minute interval until the sucrose solution of the refraction index of 1.373 is injected. Finally, the deionized water is injected into the channel chip 130 and held for 2 minutes to complete a detection cycle. Afterward, the coupling position is adjusted to 3.80 mm and 5.35 mm separately, and then the above detection procedures are repeated. As shown in FIG. 15, the detected signal strength maintains a linear relationship with the refraction index of the sample solution 400. In other words, the detection sensitivity of the double-sided grating waveguide biosensor 100 of the present invention does not change with the variations of the coupling position.

Thus, one of the features of the double-sided grating waveguide biosensor 100 of the present invention is that both using the double-sided grating structure 121 to couple in the light beam into the waveguide layer 120 and detecting the intensity of the outgoing light beam allow the light beam to possess the coupling capability within a range. Besides, the detection sensitivity of the double-sided grating waveguide biosensor 100 does not change with the variations of the angle of coupling and the coupling position.

Another feature of features of the double-sided grating waveguide biosensor 100 of the present invention is that the complexity of the detection procedures is reduced by detecting the light beam intensity of the coupling outcome.

In summation, although the present invention has been described with reference to the foregoing preferred embodiment, it will be understood that the invention is not limited to the details thereof. Various equivalent variations and modifications may still occur to those skilled in this art in view of the teachings of the present invention. Thus, all such variations and equivalent modifications are also embraced within the scope of the invention as defined in the appended claims.

What is claimed is:

1. A double-sided grating waveguide biosensor for detecting one or a plurality of properties of a sample solution, the double-sided grating waveguide biosensor at least comprising:
   a plastic grating, wherein a surface of the plastic grating is provided with a grating part;
   a waveguide layer, located on the surface of the plastic grating, wherein a part of the waveguide layer is located on the grating part to form a double-sided grating structure, and the double-sided grating structure comprises two waveguide grating parts corresponding to each other; and
   a channel chip, located on the waveguide layer, being used to guide in the sample solution, wherein when a light beam is coupled into the waveguide layer via the double-sided grating structure and propagates along the waveguide layer, wherein one of the waveguide grating parts is formed as a first surface of the double-sided grating structure and faces the channel chip, the other is formed as an opposite surface of the double-sided grating structure related to the first surface and faces the plastic gating, wherein a variation of a light beam intensity of the light beam penetrating out of the waveguide layer is detected for enabling the double-sided waveguide biosensor to detect the property of the sample solution.

2. The double-sided grating waveguide biosensor of claim 1, wherein a recognition molecule layer is fixedly bonded to the surface of the waveguide layer between the waveguide layer and the channel chip.

3. The double-sided grating waveguide biosensor of claim 1, wherein the material of the plastic grating is cyclic-olefin copolymer, polycarbonate, acrylic, or polypropene, and the material of the waveguide layer is titanium dioxide, zirconium dioxide, silicon dioxide, titanium sesquioxide, tantalum pentoxide, or zinc oxide.

4. The double-sided grating waveguide biosensor of claim 1, wherein the double-sided grating structure is provided with a coupling angle ranged from −90 to 90 degrees to couple with the light beam, and the range of the coupling angle and the coupling angle resulting in a peak value of the light beam intensity do not change with a variation of a refractive index.

5. The double-sided grating waveguide biosensor of claim 1, wherein the double-sided grating structure is provided with a coupling position, a distance between the coupling position and a terminal of the double-sided grating structure is within 0 to 2 centimeters, and the range of the coupling position and the coupling position resulting in the peak value of the light beam intensity do not change with a variation of a refractive index.

6. The double-sided grating waveguide biosensor of claim 1, wherein a sensitivity of the double-sided grating waveguide biosensor does not change with variations of a coupling angle and a coupling position.

7. A double-sided grating waveguide biosensor with sub-surface cavities for detecting one or a plurality of properties of a sample solution, the double-sided grating waveguide biosensor at least comprising:

a plastic grating, wherein a surface of the plastic grating is provided with a grating part;

a waveguide layer, located on the surface of the plastic grating, wherein a part of the waveguide layer is located on the grating part to form a double-sided grating structure, and the double-sided grating structure comprises two waveguide grating parts corresponding to each other, wherein the plastic grating has a plurality of gaps which are formed on the grating part of the surface of the plastic grating and located between the grating part and the waveguide layer; and a channel chip, located on the waveguide layer, being used to guide the sample solution, wherein when a light beam is coupled into the waveguide layer via the double-sided grating structure and propagates along the waveguide layer, wherein one of the waveguide grating parts is formed as a first surface of the double-sided grating structure and faces the channel chip, the other is formed as an opposite surface of the double-sided grating structure related to the first surface and faces the plastic grating, wherein a variation of a light beam intensity of the light beam penetrating out of the waveguide layer is detected for enabling the double-sided waveguide biosensor to detect the property of the sample solution.

8. The double-sided grating waveguide biosensor of claim 7, wherein a recognition molecule layer is fixedly bonded to the surface of the waveguide layer between the waveguide layer and the channel chip.

9. The double-sided grating waveguide biosensor of claim 7, wherein material of the plastic grating is cyclic-olefin copolymer, polycarbonate, acrylic, or polypropene, and material of the waveguide layer is titanium dioxide, zirconium dioxide, silicon dioxide, titanium sesquioxide, tantalum pentoxide, or zinc oxide.

10. The double-sided grating waveguide biosensor of claim 7, wherein the double-sided grating structure is provided with a coupling angle ranged from −90 to 90 degrees to couple with the light beam, and the range of the coupling angle resulting in a peak value of the light beam intensity does not change with a variation of a refractive index.

11. The double-sided grating waveguide biosensor of claim 7, wherein the double-sided grating structure is provided with a coupling position, a distance between the coupling position and a terminal of the double-sided grating structure is within 0 to 2 centimeters, and the range of the coupling position resulting in the peak value of the light beam intensity does not change with a variation of a refractive index.

12. The double-sided grating waveguide biosensor of claim 7, wherein a sensitivity of the double-sided grating waveguide biosensor does not change with variations of a coupling angle and a coupling position.

\* \* \* \* \*